United States Patent [19]
Ollmann, Jr.

[11] Patent Number: 5,831,098

[45] Date of Patent: Nov. 3, 1998

[54] 2-METHYL-4,4A-DIHYDRO-3H-CARBAZOLIUM SALTS AND DYES DERIVED THEREFROM

[75] Inventor: Richard R. Ollmann, Jr., Woodbury, Minn.

[73] Assignee: Minnesota Mining and Manufacturing Company, St. Paul, Minn.

[21] Appl. No.: 851,517

[22] Filed: Mar. 16, 1992

[51] Int. Cl.$^6$ .................................................. C07D 209/86
[52] U.S. Cl. ............................................................ 548/439
[58] Field of Search ............................................ 548/439

[56] References Cited

U.S. PATENT DOCUMENTS 4,942,141  7/1990  DeBoer et al. .

OTHER PUBLICATIONS

Hubschwerlen, C. and Fleury, J–P., "Dienamines Heterocycliques–II", *Tetrahedron*, vol. 33, pp. 761–765, 1977.
Kuramoto, N. et al., "Synthesis and Characterization of Deep–Coloured Squarilium Dyes for Laser Optical Recording Media," *Dyes and Pigments*, II (1989), 21–35.
Venkatataraman, K, Ed., *The Chemistry of Synthetic Dyes*, Chapter 5, Ficken, G.E., vol. IV, 1971.
M. Niaz Khan et al. "A New Route to Trinuclear Carbocyanines," *Tetrahedron*, vol. 41, No. 22, pp. 5341–5345, 1985.
R. L. Garnick et al. *J. Org. Chem.*, 1978, 43, 1226.
D. A. Cockerhill et al., *J. Chem. Soc.*, 1955, 4369.
P.M. Douglass et al., *Chem. Comm.* 1967, 343.
H–J. Teuber et al. *Tetrahedronlett*, 1965, 1703.
J. M. Babbitt et al., *Heterocyclies*, 1986, 24, 669 *ibid* 687.
O. L. Chapman et al. *J. Am. Chem. Soc.* 1971, 93, 2918.
H. Fritz et al., *Liebigs Ann. Chem.*, 1975, 1422.

Primary Examiner—Robert W. Ramsuer

[57] ABSTRACT

2-Methyl-4,4a-dihydro-3H-carbazolium salts that are useful as dye precursors and dyes derived from those precursors are disclosed. The salts are described by the formula

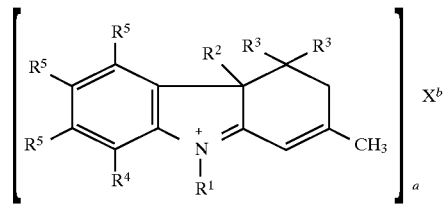

wherein $R^1$ represents an alkyl, aryl, sulfoalkyl, carboxyalkyl, sulfatoalkyl, alkoxyalkyl, acyloxyalkyl, dialkylarinoalkylene, cycloaminoalkylene, acyl, or alkenyl group having from 1 to 18 carbon atoms; $R^2$ represents an alkyl group having up to 18 carbon atoms; $R^3$ represents hydrogen or an alkyl group having from 1 to 18 carbon atoms; $R^4$ represents hydrogen or an alkyl group having from 1 to 18 carbon atoms; $R^5$ represents hydrogen, nitro, carboxyl, sulfo, hydroxy, halogen, phospho, or an alkoxy, thioalkoxy, oxyalkyl, acyl, alkyl, aryl, or amino group having up to 18 carbon atoms; wherein any two groups $R^5$, or $R^4$ and a group $R^5$, or $R^1$ and $R^4$ may together form a substituted or unsubstituted aryl, heteroaryl, aliphatic, or heteroaliphatic ring; X represents an anion; and a and b represent positive integers such that a equals b.

The salts have a partially saturated ring system that rigidifies the chromophore in the precursor and in dyes derived from it. The rigidified chromophores have narrowed absorption bands relative to corresponding non-rigid chromophores. Dyes prepared from the dye precursors of the invention typically have good solubility in non-polar solvents.

4 Claims, No Drawings

2-METHYL-4,4A-DIHYDRO-3H-CARBAZOLIUM SALTS AND DYES DERIVED THEREFROM

FIELD OF THE INVENTION

This invention relates to 3H-carbazolium dyes and precursors for their preparation.

BACKGROUND OF THE INVENTION

Dyes having chromophores containing multiple non-aromatic conjugated double bonds have been important as infrared absorbing dyes. Infrared absorbing dyes have many utilities, depending on the nature of the specific dye. These include sensitization of silver halide emulsions and photopolymers, security marking, and laser imaging.

Developing methods for extending the length of linear conjugated systems and thereby extending the wavelength response of major classes of dyes has been a long standing problem in the dye synthesis art. For example, Fischer's base (i.e., 1,3,3-trimethyl-2-methyleneindoline) is the starting material for many polymethine, cyanine, and merocyanine dyes. Recently a vinylog of Fischer's base, 1,3,3-trimethyl-2-(2-propenylidene)indoline was reported, but could not be isolated in pure form due to side reactions during its synthesis (Khan, M. N.; Fleury, J.-P.; Baumlin, P.; Hubschwerlen, C. *Tetrahedron* 1985, 41, 5341 and Hubschwerlen, C.; Fleury, J. P. *Tetrahedron* 1977, 33, 761).

U.S. Pat. No. 4,942,141 discloses infrared absorbing squarylium dyes. The formula claimed therein encompasses certain squarylium dyes related to but not included within the present invention. There is no specific teaching of the advantages achieved by providing rigidized rings within the structure according to the present invention.

SUMMARY OF THE INVENTION

This invention relates to precursors for the synthesis of rigidified dyes, the precursors being described by the formula:

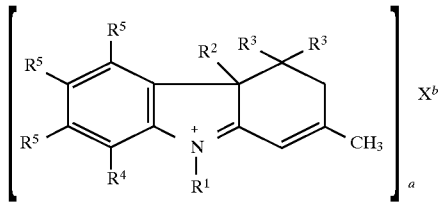

wherein $R^1$ represents an alkyl, aryl, sulfoalkyl, carboxyalkyl, sulfatoalkyl, alkoxyalkyl, acyloxyalkyl, dialkylaminoalkylene, cycloaminoalkylene, acyl, or alkenyl group having up to 18 carbon atoms; $R^2$ represents an alkyl group having from 1 to 18 carbon atoms; each $R^3$ independantly represents hydrogen or an alkyl group having from 1 to 18 carbon atoms; $R^4$ represents hydrogen or an alkyl group having from 1 to 18 carbon atoms; each $R^5$ independantly represents hydrogen, nitro, carboxyl, sulfo, hydroxy, halogen, phospho, or an alkoxy, thioalkoxy, oxyalkyl, acyl, alkyl, aryl, or amino group having up to 18 carbon atoms; wherein any two groups $R^5$, or $R^4$ and a group $R^5$, or $R^1$ and $R^4$ may together form a substituted or unsubstituted aryl, heteroaryl, aliphatic, or heteroaliphatic ring; X represents any non-interfering anion; and a and b represent positive integers such that a equals b.

In another aspect, this invention relates to rigidified dyes having the formula

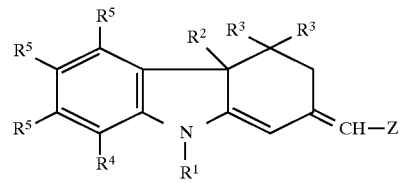

wherein $R^1$–$R^5$ are as previously defined and Z represents the atoms necessary to complete a dye selected from the group consisting of carbocyanine, azacarbocyanine, hemicyanine, styryl, diazacarbocyanine, triazacarbocyanine, diazahemicyanine, polymethinecyanine, azapolymethinecyanine, holopolar, indocyanine, merocyanine, squarylium, and diazahemicyanine dyes.

In yet another aspect, this invention relates to the free base form of the above-mentioned dye precursors having the formula

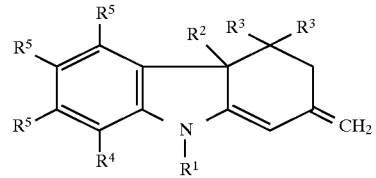

wherein $R^1$–$R^5$ are as previously defined.

The dye precursors of the present invention make possible facile preparation of long wavelength absorbing dyes that have narrower absorption bands and increased fluorescence lifetimes relative to corresponding dyes having the same or a similar chromophore in a less rigidified bonding arrangement.

The term "lower alkyl," where not further limited, refers to alkyl having from 1 to 6 carbon atoms (e.g., methyl, ethyl, propyl, isopentyl, hexyl, etc.)

The present invention incorporates an added double bond into the dye precursor that is still capable of undergoing classical dye synthesis reactions. In addition, dyes prepared from the dye precursors of present invention have other advantageous properties such as narrower absorption bands and longer fluorescence lifetimes than corresponding dyes in which the conjugated double bonds are not rotationally constrained with a fused ring system.

DETAILED DESCRIPTION OF THE INVENTION

The precursors for synthesis of rigidified dyes according to the present invention are described by the formula

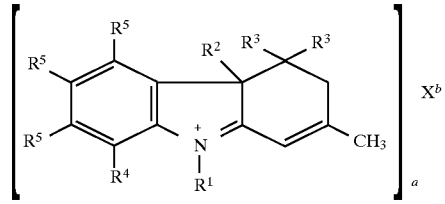

wherein $R^1$ represents (1) an alkyl group having from 1 to 18 carbon atoms and preferably a lower alkyl group having from 1 to 4 carbon atoms (e.g., methyl, ethyl, propyl, isopropyl, butyl, sec-butyl, isobutyl, tert-butyl); a sulfoalkyl group, preferably sulfo lower alkyl containing from 1 to 4 carbon atoms in the alkyl moiety (e.g., β-sulfoethyl, γ-sulfopropyl, γ-sulfobutyl, etc.); a carboxyalkyl group, preferably a carboxy lower alkyl containing from 1 to 4 carbon atoms in the alkyl moiety (e.g., β-carboxyethyl, γ-carboxypropyl, δ-carboxybutyl, etc.); a sulfatoalkyl group, preferably a sulfato lower alkyl containing 1 to 4 carbon atoms in the alkyl moiety (e.g., β-sulfatoethyl, γ-sulfatopropyl, δ-sulfatobutyl, etc.); an alkoxyalkyl group, preferably a lower alkoxy lower alkyl containing from 1 to 4 carbon atoms in both the alkoxy and alkyl moieties (e.g., β-methoxyethyl, γ-methoxypropyl, δ-propoxybutyl, etc.); an acyloxyalkyl group preferably an acyloxy lower alkyl containing from 1 to 4 carbon atoms in the alkyl moiety (e.g., acetyloxyethyl, propanoyloxyethyl, butanoyloxybutyl, benzoyloxyethyl, toluyloxypropyl, etc.); an alkoxycarbonylalkyl group, preferably a lower alkoxy carbonyl lower alkyl containing from 1 to 4 carbon atoms in both the alkoxy and alkyl moieties (e.g., β-methoxycarbonylethyl, δ-ethoxycarbonylbutyl, β-butoxycarbonylethyl, etc.); a dialkylaminoalkylene group, preferably a di-lower alkylamino lower alkylene containing from 1 to 4 carbon atoms in the alkylene and the alkyl moieties (e.g., dimethylaminoethylene, diethylaminopropylene, diethylaminobutylene, etc.); a cycloaminoalkylene group, preferably cycloamino lower alkyl containing 4 to 6 atoms in the cycloamino moiety and 1 to 4 atoms in the alkyl moiety (e.g., pyrrolidinylethylene, morpholinopropylene, piperidinebutylene, pyrrolidinylmethylene, etc.); (2) an alkenyl group (including a substituted alkenyl group), preferably a lower alkenyl containing 2 to 4 carbon atoms (e.g., ethyl, allyl, 1-propenyl, 1-butenyl, 2-butenyl, etc.); or (3) an aryl group (including a substituted aryl), such as phenyl, naphthyl, tolyl, xylyl, halophenyl (e.g., p-chlorophenyl, p-bromophenyl, etc.), alkoxyphenyl (such as methoxyphenyl, 2,4-dichlorophenyl, etc.), and an alkyl group, preferably an aryl lower alkyl containing from 1 to 4 carbon atoms in the alkyl moiety (e.g., benzyl, β-phenethyl, ω-phenbutyl, etc.).

$R^2$ represents an alkyl group having from 1 to 18 carbon atoms, preferably $R^2$ represents a lower alkyl group, more preferably $R^2$ represents methyl or ethyl;

$R^3$ represents hydrogen or an alkyl group having from 1 to 18 carbon atoms;

$R^4$ represents hydrogen or an alkyl group having from 1 to 18 carbon atoms; preferably $R^3$ represents hydrogen or lower alkyl group; more preferably $R^3$ represents hydrogen or methyl.

$R^5$ represents hydrogen, nitro, carboxyl, sulfo, halogen, phospho, or an alkoxy, carboalkoxy, carboxyalkyl, acyl, alkyl, aryl, or amino group having from 1 to 18 carbon atoms; wherein any two groups $R^5$ or $R^4$ and a group $R^5$, or $R^1$ and $R^4$ may together form a substituted or unsubstituted aryl, heteroaryl, aliphatic, or heteroaliphatic ring. Preferably, $R^5$ is hydrogen.

X represents an anion such as any non-interfering anion. Non-interfering anions include anions that will not react with the cationic dye precursor. Strong nucleophiles such as alkoxides, alkali metal amides and the like, and powerful reducing agents or oxidizing agents are interfering anions. Preferably, X may be a halide or complex halide, such as bromide, chloride, iodide, triiodide, etc.; sulfate or sulfonate (e.g., para-toluene sulfonate); phosphate or phosphonate; complex metal halides such as hexafluorophosphate, hexafluoroantimonate, tetrachlorostannate, and the like; perchlorate; nitrate; carbonate; and bicarbonate. Most preferably, X represents halide or perchlorate.

a and b represent positive integers, wherein a equals b. Preferably, a and b are 1, 2, or 3. Most preferably, a and b are 1.

The dye precursors of the present invention may be used to synthesize a wide variety of dye molecules by methods well known in the dye art and described in standard references on dye synthesis such as Hamer, F. M. *The Cyanine Dyes and Related Compounds*; Interscience Publishers: New York, 1964; and Ficken, G. E. In *The Chemistry of Synthetic Dyes*; Venkataraman, K., Ed.; Academic Press: New York, 1971; Volume IV, Chapter 5. Dyes that may be synthesized from the dye precursors of the present invention include, but are not limited to, polymethine dyes including cyanine dyes such as carbocyanine, azacarbocyanine, hemicyanine, styryl, diazacarbocyanine, triazacarbocyanine, diazahemicyanine, polymethinecyanines, azapolymethinecyanines, holopolar, indocyanine, merocyanine, squarylium, diazahemicyanine dyes.

Generally, the dye precursors of the present invention are converted to their free base form in the process of synthesizing dyes from the dye precursors. This is generally, accomplished by treatment with a base to deprotonate the dye precursor and thereby generate the free base form of the dye precursor. The base may be an inorganic base such as hydroxide or hydride ion, or the base may be an organic base, such as an amine, carboxylate ion, phenolate ion, and the like. The free base form of the dye precursors of the present invention is described by the formula

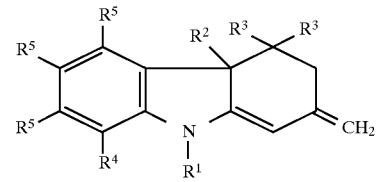

In addition to the preparation of dyes, the dye precursors of the present invention may be converted to their free base form and reacted with enamine-reactive compounds. The term "enamine-reactive" refers to materials known to react with enamines. Examples of materials which may be reacted with the free base form of the dye precursors of the present invention include, but are not limited to, α,β-unsaturated aldehydes such as acrolein (i.e., 2-propenal), 2-butenal, 2-pentenal, and the like; α,β-unsaturated esters (e.g., methyl acrylate, ethyl methacrylate, etc.; α,β-unsaturated oximes (e.g., 3-buten-2-one oxime, propenal oxime, etc.); α,β-unsaturated ketones (e.g., 3-buten-2-one, 1-penten-3-one, etc.); α,β-unsaturated nitriles (e.g., acrylonitrile); aldheydes (e.g., acetaldehyde, propanal, benzaldehyde, etc.); ketones (e.g., acetone, 2-butanone, acetophenone); esters (e.g., ethyl acetate, vinyl acetate, propyl benzoate, etc.); alkyl and aralkyl halides (e.g., 1-chlorobutane, benzyl bromide, etc.); acid halides (e.g., acetyl chloride, benzoyl bromide, acryloyl chloride, etc.); silyl halides and siloxanes (e.g., trimethylsilyl chloride, phenyldimethylsilyl chloride, octamethyltrisiloxane, etc.); etc.

Where the term "group" is used in describing substituents, substitution is anticipated on the substituent for example, alkyl group includes ether groups (e.g., $CH_3$—$CH_2$—$CH_2$—O—$CH_2$—, haloalkyls, nitroalkyls, carboxyalkyls, hydroxyalkyls, etc.) while the term alkyl or alkyl moiety includes only hydrocarbons.

EXAMPLES

The materials used in the following examples were available from standard commercial sources such as the Aldrich Chemical Company (Milwaukee, Wis.) unless otherwise noted. All compounds prepared below were characterized by one or more of the following techniques: $^1H$ nmr spectroscopy, $^{13}C$ nmr spectroscopy, infrared spectroscopy, melting point, and combustion analysis.

Example 1

This example demonstrates the preparation of 1,2,3,4,4a, 9a-hexahydro-4,4,4a,9-tetramethyl-2-oxo-9H-carbazole (1), which is useful in the preparation of compounds of the present invention.

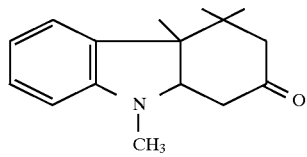

Concentrated sulfuric acid (40 ml) was added to a stirred solution of 1,3-dimethylindole (20.00 g) in 100 ml ethanol. The reaction mixture was stirred for 1 minute and 50 ml mesityl oxide was added with continued stirring. The hot black solution was stirred for 20 min and poured into a suspension of 124 g sodium carbonate monohydrate in 400 ml water. The resulting yellow solution was extracted with three 20 ml portions of ether. The ether extracts were combined and dried over anhydrous magnesium sulfate. After filtration, the ether was removed under reduced pressure. The extraction, drying, filtration, and evaporation procedure was repeated three additional times, and the isolated material was combined and vacuum distilled. The clear distillate was recrystallized to give large off-white prisms.

Example 2

This example demonstrates the preparation of 1,2,3,4,4a,9a-hexahydro-4,4,4a,9-tetramethyl-2-methylene-9H-carbazole (2), which is useful in the preparation of compounds of the present invention.

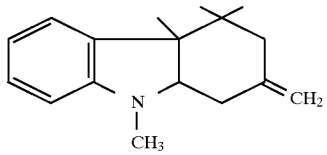

A suspension of 28.90 g (80.91 mmol) methyltriphenylphosphonium bromide and 9.06 g potassium t-butoxide (80.91 mmol) in 400 ml toluene was added in a single portion to a refluxing solution of 17.68 g (73.55 mmol) 1 in 100 ml toluene. The bright yellow mixture was stirred under reflux for one hour. The mixture was cooled and the solvent was removed under reduced pressure. The residue was combined with 500 ml hexane and filtered. The heptane solution was washed with two 200 ml portions of water, dried over anhydrous magnesium sulfate, and the solvent was removed under reduced pressure. On standing, the residue solidified to give 16.35 g of 2 as orange-yellow crystals.

Example 3

This example demonstrates the preparation of 2,4,4,4a,9-pentamethyl-4,4a-dihydro-3H-carbazolium iodide (3) which is useful as a dye precursor according to the present invention.

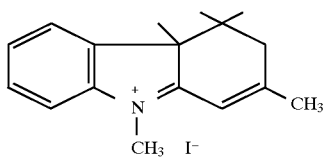

A solution of 2 (10.00 g, 41.43 mmol), 21.03 g (82.26 mmol) iodine, and 20.00 g sodium iodide in 100 ml anhydrous methanol was stirred at reflux for 4.5 hours. After partial cooling, but while the solution was still warm, 50 ml of a saturated solution of aqueous sodium thiosulfate was added to the reaction mixture. The resultant black solution was poured onto about 600 ml crushed ice. The residue was recrystallized from hot water to give 18.5 g of 3 as light yellow crystals.

Example 4

This example demonstrates the preparation of 2,4,4,4a,9-pentamethyl-4,4a-dihydro-3H-carbazolium perchlorate (4) which is useful as a dye precursor according to the present invention.

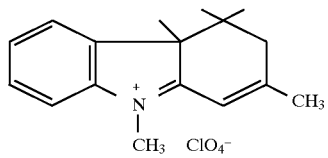

Sodium perchlorate (5.00 g) was added to a solution of 1.00 g of 3 in 20 ml boiling hot water. As the solution was allowed to cool crystals of 4 formed.

Example 5

This example describes the preparation of 2,4a-dimethyl-4,4a-dihydro-3H-carbazolium iodide (5) which is useful as a dye precursor according to the present invention.

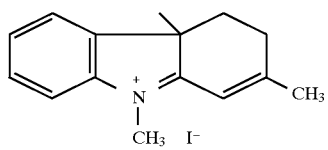

The procedures of Examples 1–3 were repeated substituting 3-butene-2-one for mesityl oxide in Example 2 to give 5.

Example 6

This example describes the preparation of 9-ethyl-4,4,4a-trimethyl-4,4a-dihydro-3H-carbazolium iodide (6) which is useful as a dye precursor according to the present invention.

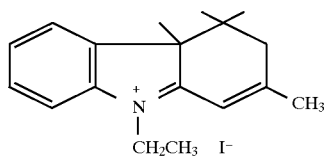

The procedures of Examples 1–3 were repeated substituting 1-ethyl-3-methylindole for 1,3-dimethylindole in Example 1 to give 6.

Example 7

This example describes the preparation of 9-ethyl-4a-methyl-4,4a-dihydro-3H-carbazolium iodide (7) which is useful as a dye precursor according to the present invention.

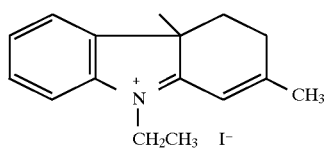

The procedures of Examples 1–3 were repeated substituting 1-ethyl-3-methylindole for 1,3-dimethylindole in Example 1 and substituting 3-butene-2-one for mesityl oxide in Example 2 to give 7.

Example 8

This example illustrates dyes that have been prepared from the dye precursors of the present invention. The dyes and methods for their preparation are listed in Table 1.

Method A: Reaction of Intermediates With Ortho Esters

A solution of dye intermediate (1 mol equivalent) and orthoester (3 mol equivalent) in pyridine was stirred under refluxing conditions for about 2 hr. The reaction mixture was cooled and the solvent removed with a rotary evaporator. The residue was taken up in a minimal amount of hot methanol, and the solution was poured into ice water. The precipitate was collected and washed with cold water.

Method B: Reaction of Intermediates With C=O,N Electrophiles

A solution of dye intermediate (1 mol equivalent) and C=O,N electrophile (1.1 mol equivalent) in pyridine was stirred under refluxing conditions for about 1 hr. The reaction mixture was cooled and the solvent removed with a rotary evaporator. The residue was taken up in a minimal amount of methanol, and the solution was poured into ice water. The precipitate was collected and washed with cold water.

Method C: Reaction of Intermediates With Squaric Acid and Croconic Acid

A suspension of dye intermediate (2.5 mol equivalent) and cyclic acid (1 mol equivalent) in a mixture of quinoline, n-butanol, and benzene (1:32:8, v:v:v) was stirred under refluxing conditions through a Dean-Stark trap for about 2 hr. The reaction mixture was cooled and the solvent removed with a rotary evaporator. The residue was taken up in water, and the resulting solid was collected and washed with water. This procedure is similar to that described by Kuramoto, N.; Natsukawa, K.; Asao, K. *Dyes & Pigments* 1989, 11, 21.

TABLE 1

| Example | Dye Structure | Synthetic Method |
|---------|---------------|------------------|
| 8 | | A |
| 9 | | A |
| 10 | | B |
| 11 | | B |
| 12 | | B |
| 13 | | B |

TABLE 1-continued
| Example | Dye Structure | Synthetic Method |
|---|---|---|
| 14 | 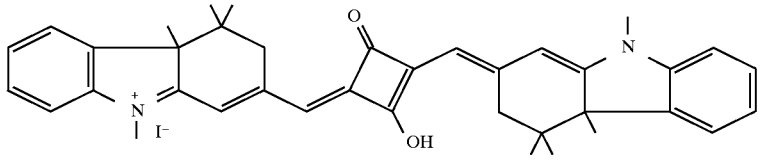 | C |
| 15 | 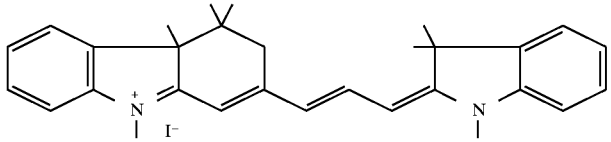 | B |
| 16 | 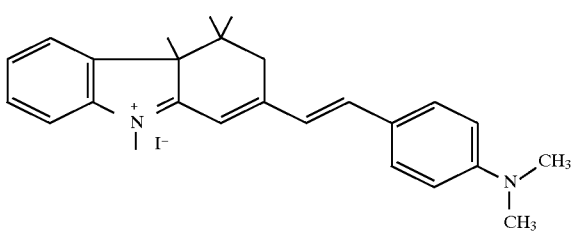 | B |
| 17 | 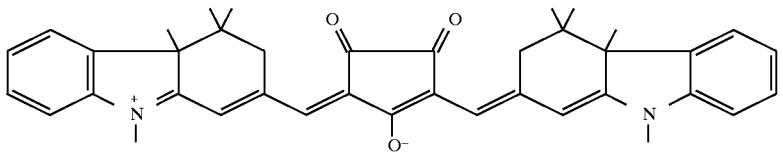 | B |
| 18 | 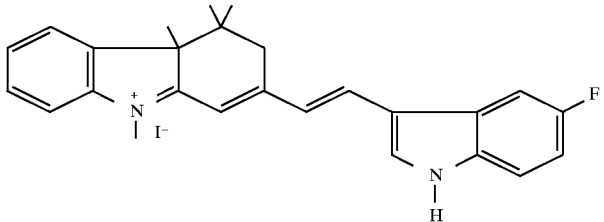 | B |
| 19 | 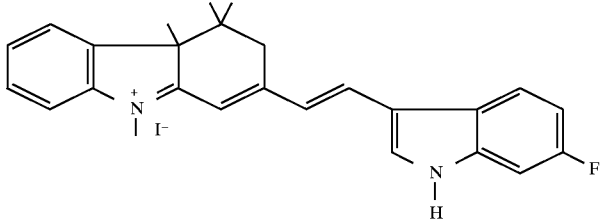 | B |
| 20 | 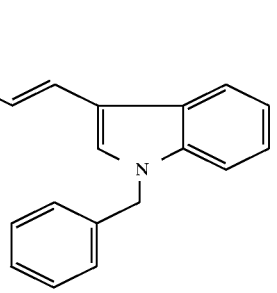 | B |

TABLE 1-continued

| Example | Dye Structure | Synthetic Method |
|---|---|---|
| 21 | | B |
| 22 | | B |
| 23 | | A |

What is claimed is:

1. A compound of the formula:

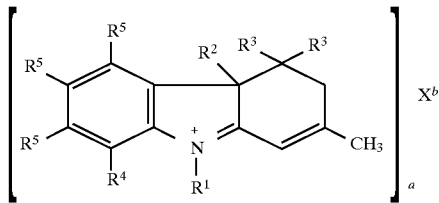

wherein $R^1$ represents an alkyl, aryl, sulfoalkyl, carboxyalkyl, sulfatoalkyl, alkoxyalkyl, acyloxyalkyl, dialkylaminoalkylene, cycloaminoalkylene, acyl, or alkenyl group having up to 18 carbon atoms;

$R^2$ represents an alkyl group having from 1 to 18 carbon atoms;

$R^3$ represents hydrogen or an alkyl group having from 1 to 18 carbon atoms;

$R^4$ represents hydrogen or an alkyl group having from 1 to 18 carbon atoms;

$R^5$ represents hydrogen, nitro, carboxyl, sulfo, hydroxy, halogen, phospho, or an alkoxy, thioalkoxy, oxyalkyl, acyl, alkyl, aryl, or amino group having up to 18 carbon atoms;

wherein any two groups $R^5$, or $R^4$ and a group $R^5$, or $R^1$ and $R^4$ may together form a substituted or unsubstituted aryl, heteroaryl, aliphatic, or heteroaliphatic ring;

X represents any non-interfering anion; and a and b represent positive integers such that a equals b.

2. A compound of claim 1 wherein $R^1$ is alkyl of 1 to 4 carbon atoms, $R^3$ is alkyl of 1 to 4 carbon atoms, and a is 1.

3. The compound of claim 1 wherein $R^2$ is methyl.

4. The compound of claim 2 wherein $R^2$ is methyl.

* * * * *